United States Patent [19]

Michaelis et al.

[11] Patent Number: 5,919,443
[45] Date of Patent: Jul. 6, 1999

[54] STABLE LYOPHILIZED PHARMACEUTICAL PREPARATIONS OF G-CSF

[75] Inventors: Uwe Michaelis; Rainer Rudolph, both of Weilheim; Gerhard Winter, Dossenheim; Heinrich Woog, Laudenbach, all of Germany

[73] Assignee: Boehringer Manheim Gmbh, Manheim, Germany

[21] Appl. No.: 08/454,186

[22] PCT Filed: Dec. 15, 1993

[86] PCT No.: PCT/EP93/03543

§ 371 Date: Jun. 15, 1995

§ 102(e) Date: Jun. 15, 1995

[87] PCT Pub. No.: WO94/14465

PCT Pub. Date: Jul. 7, 1994

[30] Foreign Application Priority Data

Dec. 18, 1992 [DE] Germany .......................... 42 42 863.7

[51] Int. Cl.⁶ ...................................................... A61K 45/05
[52] U.S. Cl. ........................................... 424/85.1; 530/351
[58] Field of Search .............................. 530/351; 424/85.1

[56] References Cited

U.S. PATENT DOCUMENTS

| 5,503,827 | 4/1996 | Woog et al. | 424/85.1 |
| 5,591,713 | 1/1997 | Igari et al. | 514/8 |
| 5,597,562 | 1/1997 | Nomura et al. | 424/85.1 |

FOREIGN PATENT DOCUMENTS

| 63146829 | 6/1988 | Japan . |
| 2193631 | 2/1988 | United Kingdom . |

*Primary Examiner*—Chhaya D. Sayala
*Attorney, Agent, or Firm*—Nikaido Marmelstein Murray & Oram, LLP

[57] ABSTRACT

The present invention concerns lyophilized pharmaceutical preparations of G-CSF that contain maltose, raffinose, sucrose, trehalose or amino sugar as stabilizing agents. In additon the invention concerns a process for the production of stabilized lyophilisates as well as the use of maltose, raffinose, sucrose, trehalose or amino sugar as stabilizing agents of pharmaceutical agents containing G-CSF.

29 Claims, No Drawings

STABLE LYOPHILIZED PHARMACEUTICAL PREPARATIONS OF G-CSF

This application is a 371 of PCT/EP93/03543 filed Dec. 15, 1993.

The present invention concerns lyophilized pharmaceutical preparations of G-CSF which contain maltose, raffinose, sucrose, trehalose or amino sugars as stabilizers. In addition the invention concerns a process for the production of these stabilized lyophilisates and the use of maltose, raffinose, sucrose, trehalose or amino sugars as stabilizers of pharmaceutical agents containing G-CSF.

Various pharmaceutical preparations which contain G-CSF (granulocyte colony stimulating factor) are already known from the state of the art.

A pharmaceutical agent containing G-CSF is described in DE 37 23 781 (GB 2,193,631) which contains at least one pharmaceutically acceptable surface-active agent, saccharide, protein or a high-molecular compound for stabilizing G-CSF. Preparations are proposed there which contain human serum albumin as a stabilizing agent. In particular preparations are stated to be advantageous which contain surface-active agents in parts by weight which correspond to 1–10000-fold the amount of G-CSF used.

Stabilized preparations of G-CSF are described in EP 0 373 679 which are characterized essentially by an acidic pH value of the solution, wherein the solutions should have as low a conductivity as possible. The solutions have a pH value of 3–3.7 in the case that the solutions contain further pharmaceutical auxiliary substances such as for example buffers or mannitol. If no buffer substances are present in the pharmaceutical formulation, pH ranges of 2.75–4 are described as being advantageous.

Furthermore, stabilized lyophilisates of human protein preparations are described in EP 0 306 824 in which stabilization is achieved by adding a mixture of urea, amino acids and detergent.

In the earlier PCT Patent Application PCT/EP92/01823 a process is described for the production of well-tolerated pharmaceutical agents containing G-CSF for infusion or injection purposes. The liquid forms of administration are characterized in particular by a low titration acidity and low buffer capacity. The pH values of the described infusion and injection solutions containing G-CSF are in an acidic range of about 3.8–4.5.

Processes for the production of liquid drug administration forms containing G-CSF which additionally contain preservatives are known from PCT/EP92/01822. The pH values of the aqueous pharmaceutical solutions are in the acidic range of 2.5–4.5. In this case the stabilization of G-CSF is essentially achieved by setting an acidic pH value which is favourable for G-CSF and by adding a mixture of various amino acids.

The previously known drug administration forms for G-CSF do, however, have some disadvantages. It was found that liquid G-CSF preparations can in some cases be sensitive towards freezing and thawing. The uncontrolled freezing and thawing of such preparations can lead to the formation of dimers, oligomers and aggregates; insoluble precipitates may also be formed. Such properties of pharmaceutical agents containing protein are questionable from a medical-pharmaceutical point of view since it is not possible to absolutely avoid an accidental freezing of the pharmaceutical solution and thus there is a risk of administering a qualitatively changed preparation.

A disadvantage of the preparations described in DE 37 23 781 is moreover that they contain pharmaceutical additives or auxiliary substances which, from a medical point of view, cannot simply be judged as harmless. Polymers and proteins have a certain potential risk with regard to their suitability as pharmaceutical additives due to their origin and their physicochemical properties. Proteins of human or animal origin as well as proteins obtained from cell cultures bear a potential residual risk of viral contaminations. Other protein-like impurities which are analytically difficult to detect can also cause immunological reactions in humans due to their antigenic properties. Moreover proteins of animal origin can generally trigger immunological reactions in humans due to their species-specific properties. Long-term reactions after a later readministration of such proteins are also possible.

The addition of high-molecular compounds (polymers) may also be problematic. Polymers can accumulate in the body due to their large molecular mass and can thus remain in the body over a long period if no biodegradation occurs. This is a particular risk in the case of subcutaneous administration since removal and distribution via the blood stream is considerably slower compared to intravenous administration. Polymers may also have antigenic properties depending on their molecular mass. In addition the purity of polymers is difficult to guarantee because of the catalysts used for their production or the presence of monomers and other polymer fragments. The use of polymers in pharmaceutical forms of administration should thus be avoided if possible in particular in the case of forms of pharmaceutical agents that can be administered subcutaneously.

The amounts of surfactant described in DE 37 23 781 must also be regarded as problematic from a medical point of view. Here surfactant concentrations are described as being advantageous in which 1 to 10000 parts by weight of a surface-active agent are present in relation to the proportion by weight of G-CSF. If, on the other hand, one considers the preferred application concentrations of G-CSF for clinical use of 0.05–1.5 mg/ml in the final pharmaceutical formulations, then this results in correspondingly high surfactant concentrations. These should be avoided from a medical point of view since they can cause local irritations.

In addition some of the known formulations have the disadvantage that, particularly in the case of subcutaneous administration, they lead to local intolerances in patients due to the low pH value used. The product obtained can cause pain and local tissue irritation in sensitive patients since the physiological pH range of 7.0–7.5 present in tissue is not adhered to.

In addition it is known from the literature that especially non-glycosylated forms of G-CSF are particuarly unstable compared to glycosylated G-CSF which is obtained from CHO cells (J. Biol. Chem. 1990, 265, 11432). The stabilization of non-glycosylated forms of G-CSF proved to be particularly difficult and requires specially selected measures in order to formulate this molecule in a stable drug administration form.

The object of the present invention was to provide a drug administration form of G-CSF which enables a proper use of G-CSF as a pharmaceutical agent and which does not have the disadvantages of the previously known drug forms described above. The pharmaceutical preparation should be stable towards uncontrolled freezing and thawing processes as well as also being stable when stored for long periods as a lyophilisate, physiologically well-tolerated, simple to use and possible to dose precisely.

The examples described in DE 37 23 781 show that stable lyophilisates can be obtained when human serum albumin is used as an auxiliary agent. The addition of sugar alcohols alone leads to less stable formulations. Therefore with regard to improving the state of the art it is desirable to find formulations which do not contain human serum albumin (HSA) or other proteins or polymers but nevertheless have a good stability even at increased temperatures. The absence of human serum albumin and polymers reduces the medical risk of side-effects such as those described for example for HSA.

Surprisingly it was found that, within the sense of the present invention, it is possible to produce stable forms of pharmaceutical agents when maltose, raffinose, sucrose, trehalose or amino sugars are used as additives.

Solid preparations which contain maltose, raffinose, sucrose, trehalose or amino sugars as auxiliary agents can be frozen or even stored at increased temperatures (up to 40° C.) with no significant loss of protein quality. The pharmaceutical quality of the active substance is not adversely affected by this. The preparations according to the invention are preferably put on the market as lyophilisates. The aqueous preparations prepared after redissolving are very well-tolerated and represent high quality preparations with regard to protein stability. In addition they have the advantage that the addition of maltose, raffinose, sucrose, trehalose or amino sugars as auxiliary agents enables solutions to be prepared with an advantageous pH value of 4–5 or 7–8 whereas the solutions known from the state of the art in general require solutions with a pH value of 2.5–3.5 for stabilizing the protein.

An additional advantage of the preparations according to the invention is that they are essentially free of protein-like or polymeric auxiliary substances the use of which may be problematic from a medical point of view. Due to the fact that liquid drug administration forms containing G-CSF obtained by dissolving lyophilisates can now be produced with a pH value of about 4–5 or 7–8, preferably with a pH value near to the pH value of blood (pH 7.2–7.4), they also have the advantage of being well tolerated and capable of administration substantially free of pain. This is particularly important for subcutaneous administration since in this case intolerances occur more easily than with intravenous administration. The preparations according to the invention can also be prepared in the clinically particularly preferred concentration ranges of 0.05–1.5 mg/ml so that it is possible to keep to injection volumes of ≦1.0 ml. Small injection volumes are particularly advantageous for subcutaneous administration since they cause only slight mechanical stimuli in the hypodermis.

A further advantage is that due to the selected auxiliary substances, the relatively high amounts of surfactant previously required in the liquid pharmaceutical preparations are no longer necessary. On the contrary low amounts of surfactant of 0.5 mg/ml or less, preferably of 0.01–0.1 mg/ml, are adequate to stabilize G-CSF. Surfactant concentrations (mg/ml) can be used advantageously which are smaller than or at most the same as the amount of G-CSF protein used per unit of volume (mg/ml). This is a particular advantage for those liquid drug forms which are intended for the subcutaneous administration of G-CSF. In addition the measures according to the invention lead to an adequate stabilization for pharmaceutical preparations of the labile non-glycosylated G-CSF molecules in particular.

The auxiliary agent maltose (malt sugar, maltobiose, 4-O-alpha-D-glucopyranosyl-D-glucose) is used in an amount of 0.01–10000-fold the amount of the active substance G-CSF. The same applies to the auxiliary substances raffinose, sucrose and trehalose. The concentration of these auxiliary substances in the liquid form of the pharmaceutical agent is 0.1–200 mg/ml, preferably 10–60 mg/ml. The stereoisomeric disaccharides cellobiose, gentiobiose or isomaltose can also be used instead of maltose. Amino sugars generally denote those monosaccharides which have an amino or an acylated amino group instead of a hydroxy group. Examples of this are glucosamine, galactosamine and neuraminic acid.

In a particular embodiment pharmaceutical preparations are provided which contain amino acids in addition to maltose, raffinose, sucrose or trehalose. Basic amino acids come into particular consideration as amino acids such as for example arginine, lysine, ornithine etc., acidic amino acids such as for example glutamic acid, aspartic acid etc. and also aromatic amino acids such as phenylalanine, tyrosine, tryptophan etc.

Amino acids are used in 0.01–10000-fold the amount of the active substance G-CSF. The concentration of these auxiliary substances in the liquid pharmaceutical preparation is 0.1–200 mg/ml, preferably 1–50 mg/ml.

In order to produce the lyophilisates, firstly the aqueous pharmaceutical solutions which contain the active substance and other common pharmaceutical auxiliary sustances are prepared. Amino acids such as e.g arginine, lysine, ornithine, phenylalanine or tyrosine come in particular into consideration as pharmaceutical auxiliary substances. In addition the aqueous preparation can contain common buffer substances such as e. g. acetic acid, hydrochloric acid, citric acid, lactic acid, tartaric acid, maleic acid and phosphoric acid or physiologically tolerated salts thereof. In the production of the auxiliary substance solution these buffer substances can either be present in the form of the corresponding free acids or in the form of the alkali, alkaline-earth or ammonium salts. The solution can in addition contain further common pharmaceutical auxiliary substances.

The sequence of addition of the various auxiliary substances or of the active substance is largely independent of the production process and is at the discretion of the person skilled in the art. The desired pH value of the solution is adjusted by adding bases such as alkali hydroxides, alkaline-earth hydroxides or ammonium hydroxide. Sodium hydroxide is preferably used for this. The adjustment of the desired pH value can in principle be achieved by adding basic solutions. In general salts of strong bases with weak acids come into consideration for this such as e.g. sodium acetate, sodium citrate, di-sodium or di-potassium hydrogen phosphate or sodium carbonate. If the pharmaceutical solution of auxiliary substance has a basic pH value, it is adjusted by titration with an acid until the desired pH range is reached. Physiologically tolerated inorganic or organic acids come into consideration as acids such as for example hydrochloric acid, phosphoric acid, acetic acid, citric acid or conventional solutions of substances which have an acidic pH value. In this respect preferred substances are salts of strong acids with weak bases such as e.g. sodium dihydrogen phosphate or potassium dihydrogen phosphate.

The concentrations of the buffer substances in the ready-to-administer liquid drug administration form are preferably about 2–80 mmol/l in each case. The total concentration of buffer substances should not exceed a value of 100 mmol/l. The concentration of buffer substances is preferably 5–40 mmol/l.

The stabilization of G-CSF molecules by means of the said auxiliary substances relates in principle to all G-CSF molecules produced by recombinant processes and variants thereof. The term G-CSF or G-CSF variant according to the present invention includes all naturally occurring variants of G-CSF as well as G-CSF proteins modified by recombinant DNA technology that are derived therefrom, in particular fusion proteins which additionally contain other protein sequences in addition to the G-CSF part. In this regard a G-CSF mutein is particularly preferred with a N-terminal Met residue at position -1 which is suitable for expression in prokaryotic cells. A recombinant methionine-free G-CSF variant which can be produced according to PCT/EP91/00192 is equally suitable. The term "G-CSF variant" is understood to include those G-CSF molecules in which one or several amino acids may be deleted or replaced by other amino acids wherein the essential properties of G-CSF are substantially retained. Suitable G-CSF muteins are described for example in EP 0 456 200.

It is expedient to add auxiliary substances which act isotonically for the production of well-tolerated parenteral drug administration forms if isotonicity cannot be already achieved by the osmotic properties of the active substance and the auxiliary substances used for stabilization. For this purpose non-ionised, well-tolerated auxiliary substances are mainly used.

It is not advantageous to add salts to adjust the isotonicity, since high concentrations of salts or ions promote the formation of G-CSF aggregates. Therefore salts are advantageously added in small amounts.

The pharmaceutical preparations can also contain further convential auxiliary substances or additives. Antioxidants such as for example glutathione, ascorbic acid or similar substances, chaotropic auxiliary substances such as for example urea and amino acids such as for example arginine, lysine, ornithine, glutamic acid and others can be added.

The invention is described in more detail in the following on the basis of representative examples of embodiments:

Examples 1–14 show in which manner lyophilisates according to the invention can be formulated, manufactured and examined in more detail with regard to the stability of the protein. The influence of the auxiliary substances added in addition to maltose, raffinose, sucrose or trehalose and of the pH value is elucidated.

Comparative experiments on lyophilisates produced on the basis of mannitol or glycine show that maltose, raffinose, sucrose or trehalose lyophilisates produce significantly better results than preparations prepared with other builders. Use of the lyophilisates described according to the invention and elucidated in the examples enables an optimal formulation to be produced for the described objective, which has a physiologically tolerated pH value, has a long-term storage stability enduring increased storage temperatures as well as mechanical stress without negative effects on the protein. The preparations are in particular not sensitive to freezing and it is possible to completely dispense with auxiliary substances that are regarded as being critical such as proteins or polymers. In addition they contain only relatively small amounts of physiologically well-tolerated surfactants.

Various sugars or sugar alcohols are examined in example 3 for their stabilizing effect in G-CSF lyophilisates. Maltose turns out to be advantageous compared to lactose and mannitol.

Lyophilisates containing maltose and further auxiliary substances are described in example 4. The results clearly demonstrate that the addition of surfactant does not substantially influence the stability of the preparation, but it prevents the adhesion of the protein to surfaces and thus prevents possible losses in content. The presence of surfactant in such formulations is thus not necessary for reasons of stabilization but rather to maintain the nominal dosage.

Various lyophilisate formulations containing maltose are compared in example 5 with two lyophilisates without maltose which are otherwise formulated identically. The data clearly show that the presence of maltose has an advantageous effect on the examined parameters with respect to stability of the preparation. The addition of further auxiliary substances such as ascorbic acid, glutathione or glutamic acid has no significant influence on the stability within the framework of the examined storage temperatures and storage periods. The preparations described in example 5 are distinguished in particular by the fact that they exhibit no changes in the examined quality criteria on long-term storage at an increased temperature.

Furthermore it is apparent from the examples that a further buffer salt is not absolutely necessary in lyophilisates which contain maltose and arginine since the arginine buffer formed when the pH is adjusted by hydrochloric acid, phosphoric acid, citric acid or other acids has an adequate pH-stabilizing effect. Arginine buffer is extremely suitable for formulating stable preparations in the pH range under 5.0 and of 7.0–7.5 (see examples 11 and 12). Example 9 shows that redissolved lyophilisates with a pH of 7.4 and containing maltose and arginine buffer are stable for at least 24 hours.

G-CSF lyophilisates are described in example 6 which contain amino sugars (galactosamine, N-methylglucosamine). It can be seen that the combination of maltose and amino sugar results in more stable preparations than the combination of glycine with amino sugars. This demonstrates that maltose in combination with physiologically well-tolerated auxiliary substances yields considerably more stable and thus higher quality lyophilisates of G-CSF with regard to pharmaceutical quality than other builders and stabilizers proposed in the literature.

Example 7 shows that G-CSF is considerably more stable in lyophilisates containing maltose than in lyophilisates containing mannitol. This is demonstrated accordingly at relevant storage temperatures and for long storage periods.

Example 8 shows that lyophilisates containing maltose at various pH values and containing various auxiliary substance additives give advantageous results compared to lyophilisates with other builders and stabilizers (sugar alcohols, amino acids).

Example 10 demonstrates the stability of the lyophilisates according to the invention containing maltose, raffinose, sucrose or trehalose after 13 weeks storage at 40° C.

Example 11 shows that the lyophilisates according to the invention are stable even with higher G-CSF concentrations and the long-term stability of the formulations according to the invention even at increased temperatures is substantiated in example 12.

EXAMPLE 1

Test Methods for the Stability Determination

The lyophilized preparations were stored in the dark at defined storage temperatures and subsequently examined with reversed phase HPLC (RP-HPLC), gel chromatography or size exclusion chromatography (SEC HPLC) and Western blot for protein purity as well as for the occurrence of aggregates and dimers. In addition the protein content was examined by OD 280 photometry, the biological activity by bioassay (NFS 60 cell test) and aggregation and precipitation by turbidity measurement. The methods used can be described as follows:

1.1 Reversed phase HPLC

The RP-HPLC was carried out using a Nucleosil C18 column (Knauer Company). The mobile phase consisted of 0.12% (v/v) trifluoroacetic acid (TFA)/water (A) and 0.1% (v/v) TFA/acetonitrile (B). The chromatography was carried out at a flow rate of 0.5 ml/min using a linear gradient of A to B.

The injection amount was 3–6 μg G-CSF depending on the formulation. It was evaluated at a wavelength of 214 nm by means of the peak area using an external standard.

1.2 Size exclusion chromatography (SEC)

A TSK G 2000 SW separation column (7.5×300 mm) was used for the SE chromatography. The separations were carried out isocratically at room temperature and a flow rate of 0.6 ml/min in a phosphate buffer (22.2 mM $Na_2HPO_4$; 107.7 mM $KH_2PO_4$; pH 6.2). The injected amount was 3–6 μg G-CSF. It was evaluated at a detection wavelength of 214 nm by means of the peak area using an external standard.

1.3 SDS page/Western blot

3 μg rhG-CSF is applied under non-reducing conditions to a 12 per cent polyacrylamide SDS gel and subjected to gel electrophoresis. Subsequently the G-CSF monomers, dimers or aggregates separated according to their molecular weight are transferred by electro-blotting onto nitrocellulose. The protein bands are identified by incubation with a specific polyclonal biotinylated anti-G-CSF antibody (PAB<GCSF>IgG) and detected by means of the phosphatase technique using streptavidin-alkaline phosphatase conjugate (SA-AP conjugate), 5-bromo-4-chloro-3-indolyl phosphate (BCIP) and nitro blue tetrazolium (NBT). The percentage amounts of monomers, dimers and aggregates are determined by laser densitometric evaluation with the aid of a series of rhG-CSF standards.

1.4 NFS-60 bioassay (biological activity)

The in vitro determination of G-CSF activity is based on the measurement of cell counts in a cell culture of NFS-60 cells stimulated by G-CSF.

Under suitable conditions it is possible to correlate the dehydrogenase activity of the cells with the concentration of G-CSF in the medium. Suitable dilutions of the G-CSF buffer solution are prepared in order to obtain a readily measurable increase in the dehydrogenase activity.

The activity is then measured photometrically at 570 and 690 nm; the reduction of the tetrazolium salt MTT (yellow) to formazan (blue) is measured.

The in vitro activity of G-CSF is calculated by comparing the data for the sample with those for the standard according to the parallel line method. The evaluation is according to the requirements of Ph. Eur. (VIII, 13).

1.5 Scattered light measurement, turbidity measurement

The measurement is carried out directly on the undiluted product solution in glass cuvettes (diameter 2 cm). The scattered light that is diffusely deflected by the liquid is measured at an angle of 90 degrees. It is measured in comparison to formazine standard suspensions according to DIN 38404C2, the values are stated in TU/F. The measurement is carried out on a suitable turbidity photometer, e.g. LTP 5 (Dr. Lange Company, Düsseldorf).

1.6 Photometry OD 280 (protein content)

The G-CSF UV spectrum has an absorbance maximum at 280 nm which is due to side chain chromophores such as tryptophan, tyrosine and phenylalanine residues. The measurement is carried out in comparison to placebo solutions by means of:

UV spectrophotometer (e.g. Uvikon 810 P or 941, Kontron Instruments)

Semi-micro quartz cuvettes, 500 μl, path length: 1 cm (e.g. Hellma, Suprasil, Cat. No. 104.002B-QS)

EXAMPLE 2

Aqueous solutions of 0.1 mg/1 ml Poloxamer 118 and 50 mg/ml of the following sugars or sugar alcohols, mannitol (formulation 1), lactose (formulation 2) and maltose (formulation 3) were admixed with G-CSF at a concentration of 70 μg/ml. After filtration through a sterilized 0.2 μm membrane filter, the solutions were filled into sterile injection bottles made of glass of hydrolytic class I. After lyophilisation they were gassed with sterile nitrogen and the stoppers which were firstly put on loosely were pressed in under aseptic conditions to close the lyophilisates. The lyophilisates were flanged and stored in the dark for 6 and 13 weeks at different temperatures. Afterwards the stability of the preparation was examined with the methods described below.

TABLE 1a

Storage at 20° C.

|  | 6 weeks storage at 20° C. | | | 13 weeks storage at 20° C. | | |
| --- | --- | --- | --- | --- | --- | --- |
|  | I | II | III | I | II | III |
| Formul. 1 mannitol | >99% | 91% | 36% | 86% | 47% | 27% |
| Formul. 2 lactose | >99% | >99% | 18% | >99% | >99% | 12% |
| Formul. 3 maltose | >99% | >99% | 6% | >99% | >99% | 7.8% |

I Purity of unchanged protein in RP HPLC
II Purity of unchanged protein in SEC HPLC
III Dimers/aggregates in Western blot TABLE 1b Storage at 40° C.

|  | 6 weeks storage at 40° C. | | | 13 weeks storage at 40° C. | | |
| --- | --- | --- | --- | --- | --- | --- |
|  | I | II | III | I | II | III |
| Formul. 1 mannitol | >81% | 70% | 50% | 69% | 25% | 70% |
| Formul. 2 lactose | >99% | >99% | 37% | >99% | >99% | not detectable/aggregated |
| Formul. 3 maltose | >99% | >99% | 6.4% | >99% | >99% | 12% |

I Purity of unchanged protein in RP HPLC
II Purity of unchanged protein in SEC HPLC
III Dimers/aggregates in Western blot

EXAMPLE 3

Lyophilisates of G-CSF were prepared. For this the auxiliary substances stated in the following table were dissolved in water for injection purposes, subsequently G-CSF was added at a concentration of 70 μg/ml and if necessary the pH value was adjusted exactly with small amounts of the buffer system. Pluronic F 68 was used as a representative of an appropriate surfactant. Other surfactants behave similarly. After sterilization by filtration through a suitable 0.2 μm membrane filter, the solutions were filled into sterile injection bottles made of glass of hydrolytic class I and lyophilized according to conventional methods. After lyophilisation they were aerated with nitrogen and the injection bottles were closed under aseptic conditions with freeze-drying stoppers. The preparations were stored in flanged bottles in the dark at defined storage temperatures for 6 and 12 weeks and examined with the methods stated in example 1.

TABLE 2

Formulations of G-CSF at pH 3.6 containing maltose

|  | Formulation 4 | Formulation 5 |
| --- | --- | --- |
| G-CSF | 70 μg | 70 μg |
| Maltose | 35 mg | 35 mg |
| L-Phenylalanine | 10 mg | 10 mg |
| Ascorbic acid | 5 mg | 5 mg |
| Glutathione | 10 mg | 10 mg |
| L-Glutamic acid | 5 mg | 5 mg |
| L-Arginine | 10 mg | 10 mg |
| Buffer (pH) | to pH 3.6 | to pH 3.6 |
| Pluronic F68 | — | 0.1 mg |
| Water for injection purposes | up to 1 ml | up to 1 ml |

TABLE 3

Storage at 20° C.

| Fm. | Storage temp. | after 6 weeks aggr. in % | after 12 weeks aggr. in % | after 6 weeks SEC % G-CSF | after 6 weeks RP % G-CSF | after 12 weeks SEC % G-CSF | after 12 weeks RP % G-CSF |
| --- | --- | --- | --- | --- | --- | --- | --- |
| 4 | +20° C. | 0.0 | 2.6 | 61 | 63 | 64 | 69 |
| 5 | +20° C. | 0.0 | 0.5 | >99 | >99 | >99 | >99 |

EXAMPLE 4

G-CSF lyophilisates containing 500 μg/ml G-CSF (formulations 6–10) were prepared as follows. The auxiliary substances stated in the following table were dissolved in water for injection purposes, G-CSF was added and if necessary the pH value was adjusted with small amounts of hydrochloric acid or disodium hydrogen phosphate. In each case 1 ml of the solutions that were previously sterilized by filtration through a 0.2 μm membrane filter were filled into injection bottles made of glass of hydrolytic glass I and freeze-dried according to conventional methods. After the lyophilisation they were aerated with nitrogen and the lyophilisates were closed under aseptic conditions with freeze-drying stoppers. The flanged lyophilisates were stored in the dark at defined temperatures and examined using the methods stated in example 1.

TABLE 4

Compositions of formulations 6–10

|  | Formul. 6 | Formul. 7 | Formul. 8 | Formul. 9 | Formul. 10 |
| --- | --- | --- | --- | --- | --- |
| G-CSF | 0.5 μg | 0.5 μg | 0.5 μg | 0.5 μg | 0.5 μg |
| Maltose | 35 mg | 35 mg | 35 mg | — | — |
| L-Phenylalanine | 10 mg | 10 mg | 10 mg | 10 mg | 10 mg |
| Ascorbic acid | 5 mg | — | — | 5 mg | — |
| Glutathione | 10 mg | — | — | 10 mg | — |
| L-Glutamic acid | 5 mg | — | — | 5 mg | — |
| L-Arginine | 10 mg | 10 mg | 10 mg | 10 mg | 10 mg |
| Buffer (pH) | to 4.5 | to 4.5 | to 6.5 | to 4.5 | to 6.5 |
| Pluronic F68 | 0.1 mg | 0.1 mg | 0.1 mg | 0.1 mg | 0.1 mg |
| Water for injection purposes | to 1 ml | to 1 ml | to 1 ml | to 1 ml | to 1 ml |

TABLE 5

Analytical results

| Form | Storage temp. | Western blot 6 w % aggr. | Western blot 12 w % aggr. | after 6 weeks SEC % G-CSF | after 6 weeks % aggr. | after 6 weeks RP % G-CSF | after 13 weeks SEC % G-CSF | after 13 weeks % aggr. | after 13 weeks RP % G-CSF |
| --- | --- | --- | --- | --- | --- | --- | --- | --- | --- |
| 6 | +8° C. | <1 | 1.0 | >99% | 0.9 | >99% | >99% | 0.7 | 99% |
|  | +40° C. | <1 | 1.7 | >99% | 0.6 | >99% | >99% | 0.6 | 98% |
| 7 | +8° C. | <1 | 1.1 | >99% | 1.6 | >99% | >99% | 1.1 | 99% |
|  | +40° C. | <1 | 2.3 | >99% | 1.9 | >99% | >99% | 1.1 | 99% |
| 8 | +8° C. | <1 | — |  |  |  | >98% | 1.5 | >99% |
|  | +40° C. | <1 | — |  |  |  | >98% | 1.4 | >99% |
| 9 | +8° C. | 3.8 | 0.3 | 95% | 5.8 | >99% | 95% | 1.5 | 98% |
|  | +40° C. | 7.9 | 2.5 | 95% | 6.4 | 93% | 86% | 0.8 | 94% |
| 10 | +8° C. | — | 5.2 |  |  |  | 96% | 1.0 | 95% |
|  | +40° C. | — | 10.3 |  |  |  | 89% | 2.6 | 89% |

EXAMPLE 5

The formulations stated in the following table (formulations 11–14) were prepared as follows: the auxiliary substances were dissolved in water for injection purposes, subsequently G-CSF was added at the stated concentration. If necessary the pH value was adjusted exactly with the aid of components of the phosphate buffer. The solutions were then filtered through a sterilized membrane filter with a pore size of 0.2 μm and filled under aseptic conditions into injection bottles of hydrolytic class I and lyophilized. After lyophilisation they were aerated with nitrogen, the lyophilisates were closed under aseptic conditions with freeze-drying rubber stoppers and flanged. The lyophilisates were stressed in the dark at defined storage temperatures. After 6 and 13 weeks they were examined with the methods stated in example 1.

TABLE 6

Lyophilisate preparations containing amino sugars

|  | Form. 11 | Form. 12 | Form. 13 | Form. 14 |
| --- | --- | --- | --- | --- |
| G-CSF | 0.5 μg | 0.5 μg | 0.5 μg | 0.5 μg |
| Pluronia F68 | 0.1 mg | 0.1 mg | 0.1 mg | 0.1 mg |
| N-methyl-glucosamine | — | 10 mg | — | 10 mg |
| Galactosamine | 10 mg | — | 10 mg | — |
| Glycine | — | — | 35 mg | 35 mg |
| Maltose | 35 mg | 35 mg | — | — |
| Phenylalanine | 10 mg | — | — | — |
| Pilosphate buffer | to pH 7.0 | to pH 7.0 | to pH 7.0 | to pH 7.0 |
| Water for injection purposes | up to 1.0 ml | up to 1.0 ml | up to 1.0 ml | up to 1.0 ml |

The analytical data obtained after storage of the aforementioned preparations are summarized in the following results table.

TABLE 7

Analytical results
DCP = decomposition products

|  |  | 6 Weeks | 12 Weeks | 12 Weeks | |
| --- | --- | --- | --- | --- | --- |
| Form. | Storage | West. blot % aggr. | West. blot % aggr. | RP-HPLC % G-CSF | % DCP in SEC HPLC |
| 11 | +8° C. | 3.8 | 2.9 | >99 | 1.2 |
|  | +40° C. | 3.2 | 2.3 | >99 | 1.8 |
| 12 | +8° C. | 1.8 | 3.8 | >99 | 1.4 |
|  | +40° C. | 1.7 | 4.5 | >99 | 0.7 |
| 13 | +8° C. | 1.1 | 1.4 | >99 | 0.9 |
|  | +40° C. | 16.8 | 13.0 | 75 | 4.2 |
| 14 | +8° C. | 1.6 | 12.4 | 97.5 | 1.2 |
|  | +40° C. | 7.7 | 26.3 | 84.5 | 3.5 |

EXAMPLE 6

Formulations 15 and 16 described in the following were prepared as follows: The stated auxiliary substances were dissolved in water for injection purposes, G-CSF was added in the stated concentration. The pH was adjusted if necessary using portions of buffer components. Afterwards the solution was filtered through a sterile membrane filter with a pore size of 0.2 μm and dispensed under aseptic conditions into sterile injection bottles made of glass of hydrolytic class I. Subsequently the injection preparations were freeze-dried, then aerated with nitrogen and the injection bottles were closed under aseptic conditions with freeze-drying stoppers and subsequently flanged. The formulations were stored in the dark at defined temperatures and examined for the parameters mentioned below. The test methods stated in example 1 were used for this.

| Formulation 15 | | Formulation 16 | |
| --- | --- | --- | --- |
| G-CSF | 0.25 | G-CSF | 0.3 mg |
| Polysorbate 80 | 0.05 mg | Polysorbate 80 | 0.1 mg |
| Phenylalanine | 5 mg | Mannitol | 50 mg |
| Maltose | 17.5 mg | Buffer | to pH 4.5 |
| L-arginine | 5 mg | Water for injection purposes | up to 1.0 ml |
| Buffer | to pH 4.5 | | |
| Water for injection purposes | up to 0.5 ml | | |

TABLE 8

Examination results after storage of
formulations 15 and 16 for 3 and 6 months

| | Formulation 15 | | | | Formulation 16 | | | |
| --- | --- | --- | --- | --- | --- | --- | --- | --- |
| | storage period 3 months | | storage period 6 months | | storage period 3 months | | storage period 6 months | |
| | 4–8° C. | 23° C. | 4–8° C. | 23° C. | 4–8° C. | 23° C. | 4–8° C. | 23° C. |
| West. blot (dimers) | 2.2 | <1% | 1.3% | 0.7 | <1% | 12% | 4.1% | 17 |
| SEC-RPLC (dimers) | <1% | <1% | <1% | <1% | <1% | 2% | <1% | 3 |
| RP-HPLC (G-CSF peak) | >99% | >99% | >98% | >98% | >99% | 98.2% | >98% | >98 |

EXAMPLE 7

The formulations described in table 9 were prepared as follows:

The stated auxiliary substances were dissolved in water for injection purposes, G-CSF was added in the stated concentration, afterwards the pH was adjusted if necessary with small portions of buffer components. The pharmaceutical solution was then filtered through a sterilized membrane filter with a pore size of 0.2 μm and subsequently dispensed into sterile injection bottles made of glass of hydrolytic class I under aseptic conditions and lyophilized.

After lyophilisation they were aerated with nitrogen and the bottles were closed under aseptic conditions with freeze-drying stoppers. The bottles were flanged and stored in the dark under defined temperature conditions. After the respective storage periods, analytical examinations were carried out using the methods described in example 1 (cf. table 10).

-continued

| mg/ml | Formulation 25 |
|---|---|
| Arginine | 10 |
| Phenylalanine | 10 |
| Hydrochloric acid | to pH 7.4 |

TABLE 9

G-CSF lyophilisates containing mannitol compared to other builders

| | Form. 17 | Form. 18 | Form. 19 | Form. 20 | Form. 21 | Form. 22 | Form. 23 | Form. 24 |
|---|---|---|---|---|---|---|---|---|
| G-CSF | 350 μg | 350 μg | 175 μg | 175 μg | 175 μg | 175 μg | 175 μg | 175 μg |
| Maltose | | | 17.5 mg | 17.5 mg | 17.5 mg | — | — | — |
| Glycine | | | | | | 4 mg | 10 mg | 8.9 mg |
| Arginine | | | 5 mg | — | 5 mg | 5 mg | — | — |
| Phenylalanine | | | 5 mg | 5 mg | 5 mg | 5 mg | — | 2.5 mg |
| Mannitol | 50 mg | 50 mg | | | | — | — | |
| Tween 80 | 0.1 mg | 0.1 mg | 0.05 mg | 0.05 mg | 0.05 mg | 0.05 mg | 0.05 mg | 0.05 mg |
| pH | 4.5 | 7.2 | 4.5 | 7.2 | 7.2 | 7.2 | 7.2 | 7.2 |
| (buffer) | HCl | phosphate | HCl | HCl | HCl | HCl | phosphate | phosphate |
| Water for injection purposes | up to 1.0 ml | up to 1.0 ml | up to 0.5 ml | up to 0.5 ml | up to 0.5 ml | up to 0.5 ml | up to 0.5 ml | up to 0.5 ml |

In Table 10 the analytical data are summarized for the stated formulations:

| | | 4 weeks | | |
|---|---|---|---|---|
| Formulation | Storage | RP-HPLC % G-CSF | SEC-HPLC % G-CSF | 4 weeks Western blot |
| 17 | 8° C. | >99 | >99 | 3.6% dimers |
| | 30° C. | 94 | 92 | 9.6% dimers |
| | 40° C. | | | 14.4% dimers |
| 18 | 8° C. | 69 | 60 | aggregates |
| | 30° C. | 44 | 36 | aggregates |
| | 40° C. | 13 | 12 | aggregates |
| 19 | 8° C. | >99 | >99 | 1.0% dimers |
| | 30° C. | >99 | 95.5 | 0.5% dimers |
| | 40° C. | >99 | 97.5 | 0.5% dimers |
| 20 | 8° C. | >99 | >99 | 1.6% dimers |
| | 30° C. | >99 | >99 | 1.4% dimers |
| | 40° C. | >99 | >99 | 2.3% dimers |
| 21 | 8° C. | >99 | >99 | 1.5% dimers |
| | 30° C. | >99 | 97.5 | 2.1% dimers |
| | 40° C. | >99 | 97 | 2.0% dimers |
| 22 | 8° C. | >99 | >99 | 2.8% di/aggr. |
| | 30° C. | 96 | 96 | 3.0% di/aggr. |
| | 40° C. | | | 12% di/aggr. |
| 23 | 8° C. | >99 | >99 | 6.8% dimers |
| | 30° C. | 91.5 | 92 | aggregates |
| | 40° C. | 79 | 74 | aggregates |
| 24 | 8° C. | >99 | >99 | 10.8% dimers |
| | 30° C. | 88 | 85 | aggregates |
| | 40° C. | 67 | 60 | aggregates |

EXAMPLE 8

Standing time of redissolved lyophilisates according to the invention having a pH of 7.4

The following composition was prepared:

| mg/ml | Formulation 25 |
|---|---|
| G-CSF | 0.35 |
| Polysorbate 80 | 0.1 |
| Maltose | 50 |

The stated auxiliary substances were dissolved in 1 ml water for injection purposes, G-CSF was added and the pH value was adjusted to pH 7.4. The solution was sterilized by filtration through a sterilized membrane filter with a pore size of 0.2 μm and afterwards dispensed into injection bottles of hydrolytic class I.

After putting on suitable freeze-drying stoppers, the preparation was freeze-dried at a main drying temperature of −25° C. and a subsequent drying temperature of +8° C. until the residual moisture reached <5%. The dried lyophilisates were aerated with nitrogen and closed.

After 6 months storage at 4–8° C. the lyophilisates were dissolved in 1 ml water for injection purposes and allowed to stand for 24 hours at room temperature.

After this standing time there was no change using the examination methods described in example 1 with regard to biological activity (NFS-60 test), protein content (photometry OD 280) and purity (Western blot), purity (SEC HPLC), purity (SDS page) and purity (RP HPLC) compared to samples examined directly after dissolution. Turbidity measurements—even under mechanical stress—resulted in very low turbidity values.

This clearly indicates that redissolved lyophilisates of the formulation according to the invention containing maltose and arginine buffer at pH 7.4 have an adequate standing time for clinical application.

EXAMPLE 9

Stability of lyophilisates according to the invention containing maltose, raffinose, sucrose or trehalose after 13 weeks storage at 40° C.

Three lyophilisates corresponding to example 8, formulation 25, were prepared that contained 50 mg/ml maltose or the same amount by weight of a) raffinose or b) sucrose or c) trehalose.

All lyophilisates were stored for 13 weeks at temperatures of 5° C., 25° C., 30° C. and 40° C., afterwards they were dissolved and examined visually and using the examination methods SEC HPLC, RP HPLC, Western blot and SDS page described in example 1.

In all cases clear colourless solutions resulted. In SEC HPLC the product peaks had a size of >98% and the dimers/aggregates had a size of <1%. In RP HPLC the product peak reached 100%, secondary peaks could not be detected, the main peak corresponded to the working standard. In SDS-page no degradation products, dimers or aggregates could be detected.

TABLE after 13 weeks storage period

| Temp. | SEC HPLC % G-CSF | RP HPLC % G-CSF | Western blot % aggregates | SDS-Page % minor bands |
|---|---|---|---|---|
| 5° C. | >98% | 100% | n.d. | <1 |
| 20° C. | >98% | 100% | n.d. | <1 |
| 30° C. | >98% | 100% | n.d. | <1 |
| 40° C. | >98% | 100% | n.d. | <1 |

EXAMPLE 10

Stability of maltose lyophilisates according to the invention containing arginine phosphate and arginine chloride buffers at pH 4.5 and pH 7.2 after 13 weeks storage at 30° C.

The following formulations were prepared according to the production process described in example 8, which only differed in their buffers and pH values:

|  | Formulation 26 | Formulation 27 | Formulation 28 | Formulation 29 |
|---|---|---|---|---|
| G-CSF | 0.35 mg | 0.35 mg | 0.35 mg | 0.35 mg |
| Polysorbate 80 | 0.1 mg | 0.1 mg | 0.1 mg | 0.1 mg |
| Phenylalanine | 10 mg | 10 mg | 10 mg | 10 mg |
| Arginine | 10 mg | 10 mg | 10 mg | 10 mg |
| Maltose | 47.5 mg | 47.5 mg | 47.5 mg | 47.5 mg |
| Phosphoric acid | to pH 4.5 | to pH 7.2 |  |  |
| Hydrochloric acid |  |  | to pH 4.5 | to pH 7.2 |

The preparations were stored at temperatures of 4 to 8° C., 20–25° C. and 30° C., dissolved after 13 weeks in 1 ml water for injection purposes and examined using the examination methods described in example 1 i.e. RP HPLC, SEC HPLC (purity) and Western blot (degradation, dimerization and aggregate formation). The results are shown in table 11 and show that the lyophilisates at pH 4.5 and 7.2 according to the invention are stable after 13 weeks storage at 30° C.

TABLE 11

Results after 13 weeks at 30° C.

|  | RP-HPLC | SEC-HPLC | Western blot | | |
|---|---|---|---|---|---|
|  | % minor peaks | | degrad. | dimers | aggregate |
| Formulation 26 | <1 | <1 | n.d. | n.d. | n.d. |
| Formulation 27 | <1 | <1 | n.d. | n.d. | n.d. |
| Formulation 28 | <1 | <1 | n.d. | <1% | n.d. |
| Formulation 29 | <1 | <1 | n.d. | <1% | n.d. | n.d. = not detectable

EXAMPLE 11

Stability of maltose lyophilisates according to the invention containing arginine phosphate and arginine chloride buffer at pH 7.4 after 4 and 13 weeks storage at 40° C.

Formulations were prepared in the same manner as described in example 8 and their pH value was adjusted to 7.4 in one case with hydrochloric acid and once with phosphoric acid.

|  | Formulation 30 | Formulation 31 |
|---|---|---|
| G-CSF | 0.35 mg | 0.35 mg |
| Polysorbate 80 | 0.1 mg | 0.1 mg |
| Phenylalanine | 10 mg | 10 mg |
| Arginine | 10 mg | 10 mg |
| Maltose | 47.5 mg | 47.5 mg |
| Phosphoric acid | pH 7.4 | |
| Hydrochloric acid | | pH 7.4 |

These two preparations were stored for 4 and 13 weeks at temperatures of 4–8° C. and 40° C. The examination results (Western blot, SDS page) after 13 weeks storage are shown in the following table 12. The results after 4 weeks storage are identical.

The results show that the maltose lyophilisates at pH 7.4 according to the invention are stable after 13 weeks storage at 40° C.

TABLE 12

Results after 13 weeks at 40° C.

|  | Stroage temp. | Western blot, non-reduc. | | SDS-Page, reduc. | | | Residual moisture % |
|---|---|---|---|---|---|---|---|
|  |  | aggr. <1% | dimers <1% | product band | degr. prod. | other bands |  |
| Form. 30 | 5° C. | n.d. | n.d. | <98% | <1% | n.d. | 1.4 |
|  | 40° C. | n.d. | n.d. | <98% | <1% | n.d. | 2.0 |
| Form. 31 | 5° C. | n.d. | n.d. | <98% | <1% | n.d. | 1.9 |
|  | 40° C. | n.d. | n.d. | <98% | <1% | n.d. | 2.1 |

EXAMPLE 12

Stability of lyophilisates according to the invention having a pH of 7.4 and G-CSF concentrations of 0.5 and 1.0 mg/ml after 13 weeks storage at 40° C.

The following formulations were prepared according to the production process described in example 8 which differ in their content of G-CSF:

| mg/ml | Formulation 32 | Formulation 33 |
|---|---|---|
| G-CSF | 0.5 mg | 1.0 mg |
| Polysorbate 80 | 0.1 mg | 0.1 mg |
| Phenylalanine | 10 mg | 10 mg |
| Arginine | 10 mg | 10 mg |
| Maltose | 47.5 mg | 47.5 mg |
| Phosphoric acid | pH 7.4 | pH 7.4 |

The formulations were stored for 4 weeks and 13 weeks at −20° C., 4–8° C., 20° C.–25° C., 30° C. and 40° C., afterwards dissolved in 1 ml water for injection purposes and examined using the examination methods SEC HPLC, RP HPLC, Western blot and SDS-page described in example 1 (examination results see table 13).

The results show that the lyophilisates of the formulations according to the invention are stable even at a higher protein concentration of up to 1 mg/ml after 13 weeks storage at 40° C.

EXAMPLE 14

Long-term stability during 9 months

Lyophilisates were prepared using formulation 31 of example 11 and the preparations were stored for 9 months at temperatures of −20° C., 5° C., 25° C., 30° C. and 40° C. and examined after 3, 6 and 9 months using all examination methods described in example 1.

No change could be detected in any of the examined parameters during the storage period. At the end of the storage periods and at all temperatures the preparation proved to be fully biologically active, it had the complete protein content and showed bands or peaks in all determinations of purity which were well below 1% of the intact G-CSF molecule.

The results show that lyophilisates according to the invention are stable even when stored for long periods at higher temperatures and thus greatly exceed the stabilites described in the state of the art.

TABLE 14

| | Storage at 30° C. | | |
|---|---|---|---|
| | 3 months | 6 months | 9 months |
| NFS 60 test 80–125% | corresponds | corresponds | corresponds |
| OD 280 | 358 mg | 360 mg | 352 mg |

TABLE 14-continued

| | Storage at 30° C. | | |
|---|---|---|---|
| | 3 months | 6 months | 9 months |
| SDS page minor bands Western blot | <1% | <1% | <1% |
| % aggregates | n.d. | n.d. | n.d. |
| % dimers RP HPLC | <1% | <1% | <1% |
| Product peak SEC HPLC | >99% | >99% | >99% |
| Product peak | >98% | >98% | >98% |
| Minor peaks | n.d. | n.d. | n.d. |
| Turbidity measurement TU/F | 0.5 | 0.5 | 0.5 |

TABLE 13

| | Formulation 32 | | | | | |
|---|---|---|---|---|---|---|
| Test parameter | 0 weeks [refrigerator] | 13 weeks [−20° C.] | 13 weeks [refrigerator] | 13 weeks [RT] | 13 weeks [30° C.] | 13 weeks [40° C.] |
| Visual examination | | | | | | |
| appearance, lyophilisate | — | white | white | white | white | white |
| clarity, (solution) | — | clear | clear | clear | clear | clear |
| SEC-HPLC | | | | | | |
| [purity %] | >98 | >98 | >98 | >98 | >98 | >98 |
| [dimers/aggregates %] RP-HPLC | | | | | | |
| [purity %] | >98 | >98 | >98 | >98 | >98 | >98 |
| [sum of minor peaks %] | <1 | <1 | <1 | <1 | <1 | <1 |
| Western blot | | | | | | |
| [dimers %] | n.d. | n.d. | n.d. | n.d. | n.d. | n.d. |
| [aggregates %] | n.d. | n.d. | n.d. | n.d. | n.d. | n.d. |
| [degradation products %] | n.d. | n.d. | n.d. | n.d. | n.d. | n.d. |
| SDS-PAGE, silver stain | | | | | | |
| [monomers %] | — | >>99% | >>99% | >>99% | >>99% | >>99% |
| [additional bands %] | — | n.d. | n.d. | n.d. | n.d. | n.d. |
| [degradation products %] | — | <<1% | <<1% | <<1% | <<1% | <<1% |

| | Formulation 33 | | | | | |
|---|---|---|---|---|---|---|
| Test parameter | 0 weeks [refrigerator] | 13 weeks [−20° C.] | 13 weeks [refrigerator] | 13 weeks [RT] | 13 weeks [30° C.] | 13 weeks [40° C.] |
| Visual examination | | | | | | |
| appearance, lyophilisate | — | white | white | white | white | white |
| clarity, (solution) | — | clear | clear | clear | clear | clear |
| SEC-HPLC | | | | | | |
| [purity %] | >98 | >98 | >98 | >98 | >98 | >98 |
| [dimers/aggregates %] RP-HPLC | | | | | | |
| [purity %] | >98 | >98 | >98 | >98 | >98 | >98 |
| [sum of minor peaks %] | <1 | <1 | <1 | <1 | <1 | <1 |

-continued

| | Formulation 33 | | | | | |
|---|---|---|---|---|---|---|
| Test parameter | 0 weeks [refrigerator] | 13 weeks [−20° C.] | 13 weeks [refrigerator] | 13 weeks [RT] | 13 weeks [30° C.] | 13 weeks [40° C.] |
| Western blot | | | | | | |
| [dimers %] | n.d. | n.d. | n.d. | n.d. | n.d. | n.d. |
| [aggregates %] | n.d. | n.d. | n.d. | n.d. | n.d. | n.d. |
| [degradation products %] | n.d. | n.d. | n.d. | n.d. | n.d. | n.d. |
| SDS-PAGE, silver stain | | | | | | |
| [monomers %] | — | >>99% | >>99% | >>99% | >>99% | >>99% |
| [additional bands %] | — | n.d. | n.d. | n.d. | n.d. | n.d. |
| [degradation products %] | — | <<1% | <<1% | <<1% | <<1% | <<1% | n.d. = not detectable

We claim:

1. A process for the production of lyophilized, storage stable, pharmaceutical preparations of G-CSF for injection or infusion solutions, said process comprising
    preparing an aqueous solution containing G-CSF and a stabilizing amount of at least one stabilizing agent selected from the group consisting of maltose, cellobiose, gentiobiose, isomaltose, and sucrose, wherein said aqueous solution has a pH of 7–8,
    adding a physiologically tolerated amount of a surfactant to said aqueous solution, wherein said surfactant is in an amount no greater than the amount of G-CSF in the solution, and
    thereafter lyophilizing the aqueous solution,
    wherein said preparation is reconstituted prior to administration by injection or infusion, and wherein said preparation is essentially free of human serum albumin and polymers.

2. The process of claim 1, wherein the stabilizing agent is maltose or sucrose.

3. The process of claim 2, wherein the stabilizing agent is maltose.

4. The process of claim 3, wherein said maltose is in an amount less than 0.5 mg/ml.

5. The process of claim 4, wherein said amount is 0.01–0.1 mg/ml.

6. The process of claim 1, wherein a physiologically tolerated amount of at least one amino acid is added to the aqueous solution.

7. The process of claim 6, wherein the amino acid is arginine and/or phenylalanine.

8. The process of claim 1, wherein at least one of antioxidants, complexing agents, buffers, acids, bases and isotonizing agents are added to the aqueous solution.

9. The process of claim 1, wherein phosphate buffer or acetate buffer is added to the aqueous solution.

10. The process of claim 1, wherein arginine phosphate buffer, arginine chloride buffer or arginine citrate buffer is added to the aqueous solution.

11. The process according to claim 1, wherein said preparation is devoid of non-G-CSF proteins.

12. The process according to claim 1, wherein said G-CSF retains more than 99% activity after storage at 20° C. for 13 weeks.

13. A method of avoiding the loss of quality of G-CSF during freezing or during storage at increased temperature, and at least substantially avoiding the occurrence of aggregates and dimers of G-CSF after redissolution of a lyophilisate, said method comprising adding to the G-CSF a stabilizing amount of a stabilizing agent selected from the group consisting of maltose, cellobiose, gentiobiose, isomaltose and sucrose, wherein said G-CSF is in a solution with a pH of 7–8.

14. A lyophilized and reconstituted pharmaceutical preparation comprising G-CSF, a stabilizing amount of a stabilizing agent selected from the group consisting of maltose, cellobiose, gentiobiose, isomaltose and sucrose and a physiologically tolerated amount of surfactant, said amount of surfactant being no greater than the amount of G-CSF in the preparation, wherein said preparation is reconstituted at a pH of 7–8 prior to administration by injection or infusion and wherein said preparation is devoid of human serum albumin and polymers.

15. The preparation of claim 14, wherein the stabilizing agent is maltose or sucrose.

16. The preparation of claim 15, wherein the stabilizing agent is maltose.

17. Preparation of claim 16, wherein said amount is less than 0.5 mg/ml.

18. Preparation of claim 17, wherein said amount is 0.01–0.1 mg/ml.

19. The preparation of claim 14, wherein a physiologically tolerated amount of at least one amino acid is in the preparation.

20. Preparation of claim 19, wherein the amino acid is arginine and/or phenylalanine.

21. Preparation of claim 14, further comprising at least one of antioxidants, complexing agents, buffers, acids, bases and isotonizing agents.

22. Preparation of claim 14, further comprising a phosphate buffer or acetate buffer.

23. Preparation of claim 14, further comprising arginine phosphate buffer, arginine chloride buffer or arginine citrate buffer.

24. Preparation of claim 14 wherein the preparation is essentially free of non-G-CSF proteins.

25. An aqueous pharmaceutical preparation obtained by redissolution of the lyophilized preparation of claim 14.

26. The aqueous preparation of claim 25, wherein the pH is 7.0–7.5.

27. The preparation of claim 14, wherein the stabilizing agent is selected from the group consisting of maltose, cellobiose, gentiobiose and isomaltose.

28. The preparation of claim 14, wherein the stabilizing agent is sucrose.

29. The preparation according to claim 14, wherein said G-CSF retains more than 99% activity after storage at 20° C. for 13 weeks.

* * * * *